United States Patent [19]

Webler

[11] Patent Number: 4,796,640

[45] Date of Patent: Jan. 10, 1989

[54] APPARATUS WITH FAST RESPONSE THERMISTOR

[75] Inventor: William E. Webler, Santa Ana, Calif.

[73] Assignee: American Hospital Supply Corporation, Evanston, Ill.

[21] Appl. No.: 570,619

[22] Filed: Jan. 13, 1984

[51] Int. Cl.$^4$ ............................................. H61B 5/02
[52] U.S. Cl. .................................... 128/736; 128/692; 128/713; 73/204.21
[58] Field of Search ...................... 128/736, 692, 713; 604/53, 246; 73/204

[56] References Cited

U.S. PATENT DOCUMENTS

| | | | |
|---|---|---|---|
| 3,595,079 | 7/1971 | Grahn | 128/692 |
| 3,995,623 | 12/1976 | Blake et al. | 128/2.06 E |
| 4,105,022 | 8/1978 | Antoshkiw et al. | |
| 4,153,048 | 5/1979 | Magnini | 128/692 |
| 4,230,126 | 10/1980 | Elings | 128/692 |
| 4,236,527 | 12/1980 | Newbauer et al. | 128/692 |
| 4,263,921 | 4/1981 | Trugillo | 128/736 |
| 4,328,806 | 5/1982 | Cooper | 128/642 |
| 4,329,994 | 5/1982 | Cooper | |
| 4,476,877 | 10/1984 | Barker | 128/736 |
| 4,502,488 | 3/1985 | Degironimo et al. | 128/692 |

Primary Examiner—Edward M. Coven
Attorney, Agent, or Firm—Gordon L. Peterson

[57] ABSTRACT

An apparatus for measuring the temperature of a fluid flowing within a body comprising an elongated tube sized to be received within a vein or an artery and having a peripheral wall, at least one lumen extending longitudinally within the tube and an opening in the peripheral wall which extends from the lumen to the exterior of the tube. A thermistor is mounted in the lumen adjacent the opening by a thermistor mounting body. The thermistor mounting body cooperates with the tube to at least partially define a cavity at the opening which opens radially outwardly. The thermistor is partially in the mounting body and projects radially outwardly of the mounting body into the cavity so that the portion of the thermistor which projects into the cavity is in good heat transfer relationship to the fluid flowing within the body. The thermistor has a major axis and a minor axis, and the major axis is generally transverse to the direction of the flowing fluid. The tube has a body line, and the thermistor extends radially outwardly no farther than about the body line.

19 Claims, 3 Drawing Sheets

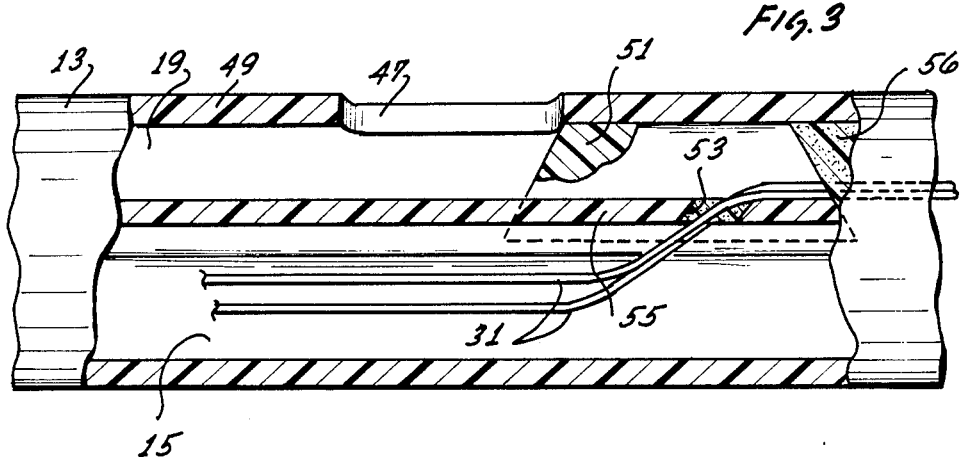
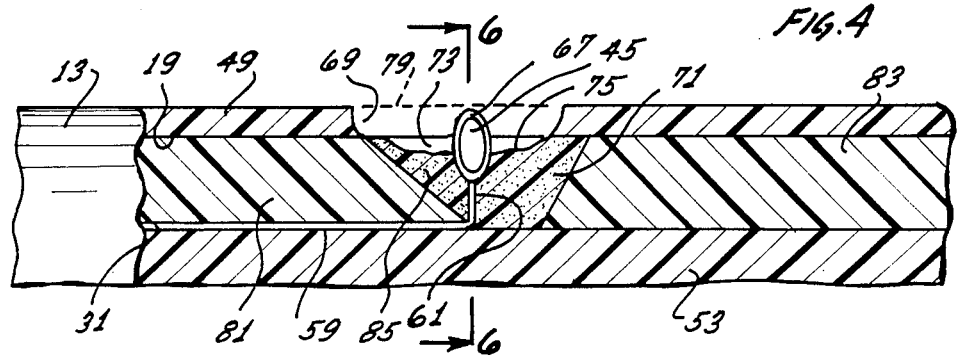
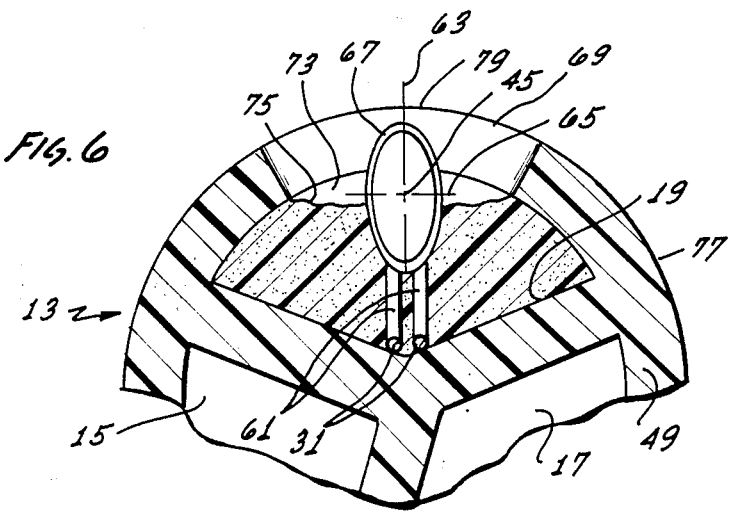

APPARATUS WITH FAST RESPONSE THERMISTOR

BACKGROUND OF THE INVENTION

Various medical procedures require the measurement of the temperature of a fluid, such as blood, flowing within a body. For example, to make thermodilution measurements, a bolus of cold liquid is injected into the right atrium or vena cava, and the resulting change in blood temperature is measured in the pulmonary artery. The temperature measurement is made by a thermistor which is carried by a thermodiulation catheter. U.S. Pat. Nos. 3,995,623; 4,105,022; and 4,329,994 show different techniques for mounting a thermistor on a catheter.

Thermodilution blood temperature measurements do not require that the thermistor have a very rapid response. However, for some medical procedures, such as the calculation of ejection fraction, it is necessary to measure changes in blood temperature as they occur. In this event, it is necessary or desirable that the thermistor measure blood temperature directly rather than the temperature of the catheter on which it is mounted. Specifically, the thermistor should follow the beat-to-beat blood temperature changes so that discrete steps in the temperature curve can be observed. Unfortunately, the patented constructions identified above prevent the thermistor from having an adequately rapid response.

SUMMARY OF THE INVENTION

This invention provides for the mounting of a thermistor so that it has a very rapid response. With this invention, the thermistor can track temperature changes about one-half as rapidly (twice the effective time constant) as the thermistor could track temperature changes if it were not mounted on a probe or catheter-type carrying apparatus. Conventional thermistor mounts typically respond less than one twentieth (1/20) as rapidly (20 times the effective time constant) as an unmounted thermistor.

The apparatus of this invention, which may be, for example, a probe or a catheter, includes an elongated tube sized to be received within a vein or artery and having proximal and distal ends, a peripheral wall, at least one lumen extending longitudinally within the tube and an opening in the peripheral wall which extends from the lumen to the exterior of the tube. In order to follow the increments of temperature change, a thermistor is mounted in an essentially exposed condition adjacent the opening of the tube. The thermistor can advantageously be mounted by a thermistor mounting body located in the lumen adjacent the opening. The thermistor mounting body cooperates with the tube to at least partially define a cavity which opens radially outwardly at the opening. In order to expose the thermistor, the thermistor is only partially within the mounting body and projects radially outwardly of the mounting body into the cavity. To assure that the fluid flowing along the tube can contact the projecting portion of the thermistor, the cavity is much larger than the thermistor so that the thermistor is spaced from the wall of the cavity over a major area of the cavity. Accordingly, the portion of the thermistor which projects into the cavity is in good heat transfer relationship to the fluid, the temperature of which is to be measured.

The thermistor has a major or long axis and a minor or short axis. To further assist in providing the thermistor with a rapid response, the thermistor is preferably mounted with the major axis generally transverse to the adjacent portions of the longitudinal axis of the lumen. For optimum results, the major axis extends perpendicular to the axis of the lumen and generally perpendicular to the direction of fluid flowing along the tube.

To make the thermistor saline resistant, a relatively thin layer of insulating material preferably covers at least the portion of the thermistor which is in the cavity. This layer is made as thin as possible so as to minimize the extent to which it reduces heat transfer between the fluid and the thermistor. Thus, this layer is substantially thinner than the mounting body. The mounting body is preferably constructed of a material having good heat insulation properties so as to retard heat transfer between the thermistor and the other portions of the apparatus. Accordingly, the thermistor is made of respond essentially, or primarily, to temperature changes to the fluid and only to a very minimal degree to temperature changes of the apparatus.

The thermistor is typically a small and somewhat fragile element. To protect the thermistor from shearing off when, for example, the apparatus is withdrawn from a tubular introducer, the thermistor preferably does not extend radially outwardly of the cavity. Stated differently, the tube has a body line, and the thermistor extends radially outwardly no further than about such body line.

In a preferred construction, the apparatus also includes first and second plugs in the lumen on opposite sides of the mounting body, and the mounting body at least assists in retaining the plugs in the lumen. To securely mount the thermistor and to provide adequate saline protection without covering too much of the thermistors exterior surface, the mounting body preferably covers no more than about one half of the exterior surface of the thermistor.

In a preferred construction, the apparatus includes at least one thermistor lead coupled to the thermistor. The lead has an axial portion which extends along the lumen and radial portion joined to the axial portion and extending generally transverse to the axial portion at the cavity. The radial portion is joined to the thermistor. In this fashion, the thermistor can be mounted with its major axis extending generally transverse to the axis of the lumen.

The invention, together with additional features and advantages thereof, may best be understood by reference to the following description taken in connection with the accompanying illustrative drawings.

BRIEF DESCRIPTION OF THE DRAWINGS

FIGS. 3–5 are enlarged, longitudinal sectional views taken on an axial plane illustrating the portions of the catheter adjacent the injectate port, the thermistor, and balloon, respectively. FIG. 4 is taken generally along line 4—4 of FIG. 2.

FIG. 6 is an enlarged fragmentary sectional view taken generally along line 6—6 of FIG. 4.

DESCRIPTION OF THE PREFERRED EMBODIMENTS

Figures 1, 2:
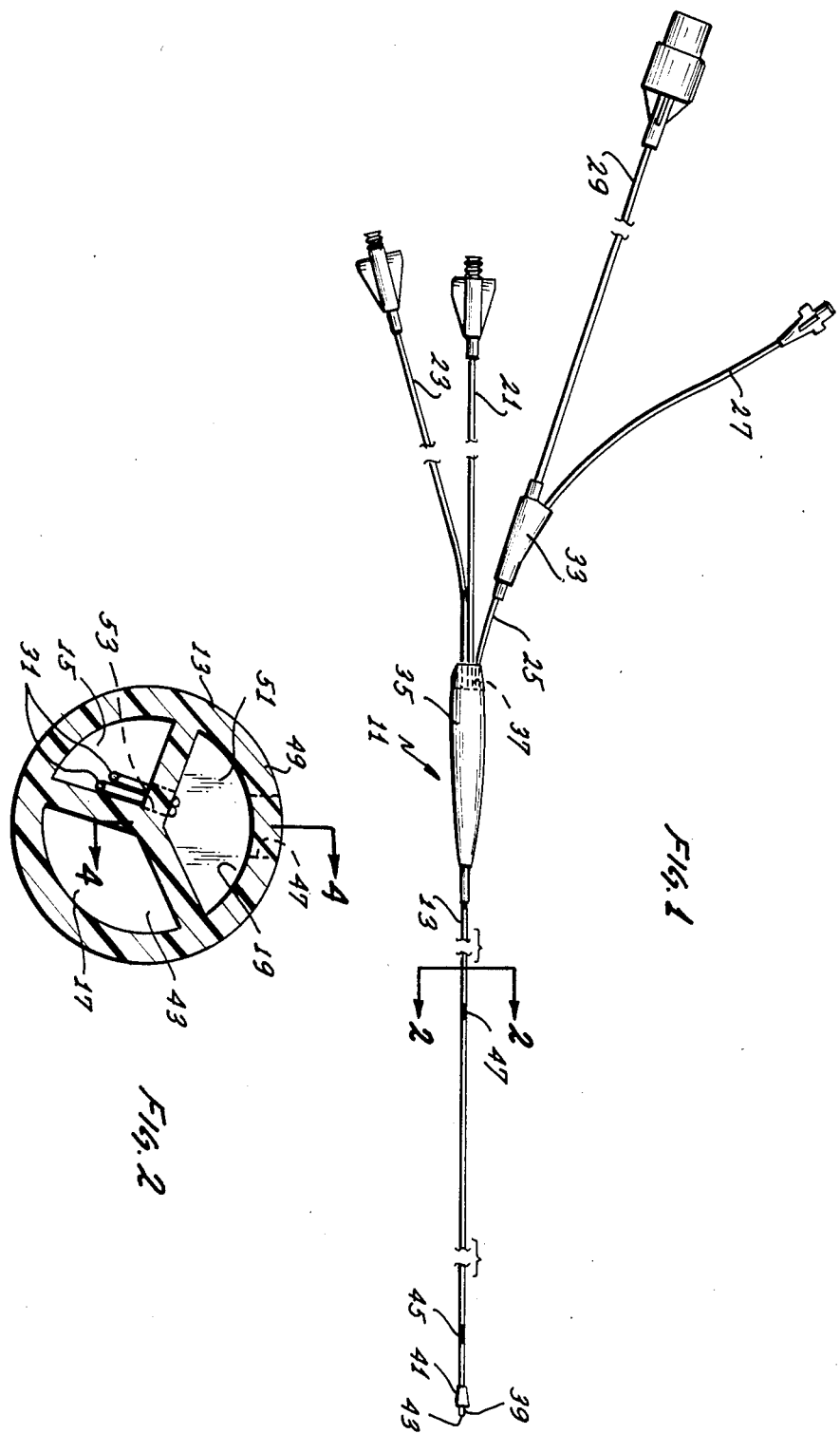
FIG. 1 is an elevational view of a catheter constructed in accordance with the teachings of this invention.
FIG. 2 is an enlarged sectional view taken generally along line 2—2 of FIG. 1.

FIG. 1 shows an apparatus in the form of a catheter 11 which comprises an elongated catheter tube 13 having a balloon inflation lumen 15 (FIG. 2), a through lumen 17 and an injectate lumen 19. A pressure monitoring tube 21 and an injectate tube 23 are fused to the tube 13 within the through lumen 17 and the injectate lumen 19, respectively. A tube 25 is fused to the tube 13 within the lumen 15 and is joined to an inflation tube 27 and a conduit 29 for thermistor leads 31 by a coupler 33. The proximal end of the catheter tube 13 and the distal end of the tubes 21, 23 and 25 are encased by a flexible sleeve 35.

The catheter tube 13 may be extruded from a suitable biocampatible plastic material. The catheter tube 13 is flexible, elongated and sized to be received within a vein or an artery. The catheter tube 13 has a proximal end 37 and a distal end 39.

The balloon inflation lumen 15 extends continuously from the proximal end 37 through a port 40 (FIG. 5) to a balloon 41 closely adjacent the distal end 39. The balloon 41 and the manner in which it is inflated through the balloon inflation lumen 15 is conventional.

Figure 5:
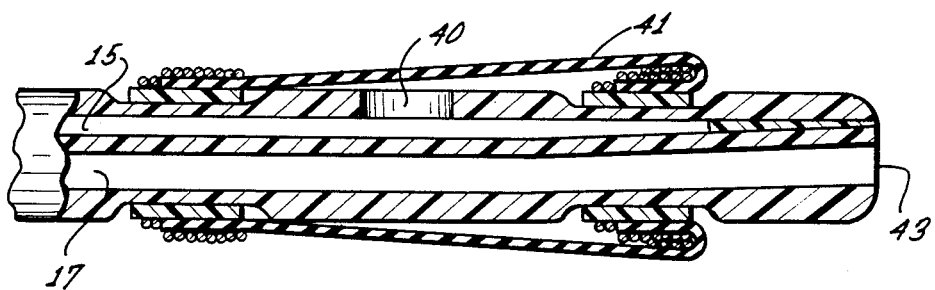

The through lumen 17 extends continuously from the proximal end 37 to the distal end 39 where it opens at a distal port 43 (FIG. 5). The through lumen 17 can be used, for example, to monitor pressures within the body.

The injectate lumen 19 extends continuously from the proximal end 37 to a location distally of a thermistor 45. For example, the thermistor may be 1.45 inches to 1.65 inches from the distal end 39. An injectate port 47 (FIGS. 1 and 3) extends through a peripheral wall 49 of the catheter tube 13 to provide communication between the injectate lumen 19 and the exterior of the tube. Accordingly, a liquid injectate can be injected through the injectate tube 23, the injectate lumen 19 and the injectate port 47 into the patient. For example, the injectate port 47 may be 8.17 inches to 8.37 inches from the distal end 39. Of course, the catheter 11 can be provided with additional lumens, if desired, to provide additional functions for the catheter.

A plug 51 of a suitable plastic material and a mass of urethane adhesive 56 are provided in the injectate lumen 19 just distally of the injectate port 47 to completely close off the lumen 19 distally of the injectate port. In this example, the thermistor leads 31 extend from the conduit 29 through the tube 25 and the balloon inflation lumen 15 to a location adjacent the plug 51. From there, the leads 31 pass through a sealed opening 53 in a partition 55 between the lumens 15 and 19 and between the plug 51 and the partition 55 into the injectate lumen 19 distally of the plug. Of course, the cross over of the leads 31 between lumens is optional.

The leads 31 extend through the lumen 19 to the thermistor 45 as shown in FIG. 4. Each of the leads 31 has an axially extending portion 59 which extends axially of the lumen 19 and a radially extending portion 61 which extends perpendicular to the portions 59 and joins the portions 59 to the thermistor 45.

Thermistor 45, which in this embodiment is a bead-type thermistor, has a major axis 63 and a minor axis 65 (FIG. 6), with the major axis being much longer in this embodiment than the minor axis. The major axis 63 is generally parallel to the radially extending portions 61. The thermistor 45 is completely covered with, and encapsulated in, a thin layer 67 of electrical insulating material, such as one or more thin coatings of vinyl and/or urethane to provide saline protection.

The peripheral wall 49 has an opening 69, and the thermistor 45 is mounted in a radially extending zone which includes this opening. The thermistor 45 is mounted by a mounting body 71 which is in the lumen 19 adjacent the opening 69. The mounting body 71 cooperates with the tube 13 to define a cavity 73 at the opening 69 which opens radially outwardly.

The mounting body 71 may be constructed of urethane or other suitable biocompatible electrical and thermal insulating adhesive material. The thermistor 45 is partially within the mounting body 71 and projects radially outwardly of the mounting body into the cavity 73. The cavity 73 has an outer wall 75 and the cavity 73 is much larger than the thermistor 45 so that the thermistor 45 is spaced from the wall 75 of the cavity over a major area of the wall. Thus, only a very small percent of the volume of the cavity 73 is occupied by the thermistor. The thermistor 45 is greatly enlarged in FIGS. 4 and 6 for clarity. The opening 69 and the cavity 73 are sufficiently large so that fluid flowing along the tube 13 can readily flow over the portion of the thermistor 45 which projects radially outwardly of the mounting body 71. Because the projecting portion of the thermistor 45 is covered only by the thin layer 67, the projecting portion of the thermistor is in good heat transfer relationship to the fluid flowing along the tube 13.

As shown in FIGS. 4 and 6, the thermistor 45 is mounted with the major axis 63 extending perpendicular to the longitudinal axis of the lumen 19 and, hence, generally transverse to the fluid flowing along the tube 13. Accordingly, the thermistor 45 projects as far as possible into the fluid stream flowing along the tube 13, and maximum heat transfer is obtained.

The peripheral wall 49 has an outer peripheral surface 77, and the outline of that surface over the opening 69 is a body line 79 of the tube 13. The thermistor 45 extends radially outwardly no farther than about the body line 79 and, in the embodiment illustrated, lies slightly radially inwardly of the body line. Thus, the thermistor 45 does not extend out of the cavity 73.

Plugs 81 and 83 (FIG. 4) are provided in the lumen 19 in opposite sides of the mounting body 71. The plugs 81 and 83 completely block the lumen 19 on opposite sides of the opening 69, and the plug 81 has a sharply inclined face 85 which provides ample room for the radially extending portions 61 of the thermistor leads 31.

Because the mounting body 71 is constructed of an adhesive material, it can be used to adhere the plugs 81 and 83 in position. Specifically, the plugs 81 and 83 are inserted into the lumen 19, and after the thermistor 45 is in position, the adhesive is poured between the plugs around the thermistor and allowed to cure to form the mounting body 71. The plugs 81 and 83 serve to confine the mounting body 71 while it is curing. By constructing the mounting body 71 of an adhesive material which will strongly bond to the layer 67, and preferably the same adhesive insulating material which forms the outer portions of the layer 67, a saline-tight joint is formed between the mounting body and the layer 67 which prevents the ingress of saline.

The mounting body 71 covers no more of the exterior surface area of the thermistor 45 than is necessary to mount the thermistor and to provide saline protection. In the embodiment illustrated, the mounting body 71 convers no more than about one half of the exterior surface of the thermistor.

The mounting body 71 thermally insulates the thermistor 45 from the adjacent portions of the catheter 11, i.e., the plugs 81 and 83 and the partition 55. The thin layer 67 on the projecting portion of the thermistor 45 is many times thinner than the mounting body 71. The thermistor 45 should be a fast response thermistor when mounted and preferably has a response time which is rapid enough to pressure the temperature changes within the interval between heart beats. For example, an average mounted response time to 100 to 150 milliseconds or less should be adequate.

In use of the catheter 11, the catheter tube 13 is introduced through a vein or artery of a patient and into the heart (FIG. 7) using known techniques. The balloon 41 is inflated through the balloon inflation lumen 15 and the port 40, and the inflated balloon is used to carry the distal end 39 of the catheter 11 to the desired location. In the example shown in FIG. 7, the balloon 41 is carried into the pulmonary artery 87. Because the thermistor 45 is below the body line 79, it will not rub against any introducer which is used, either during the insertion or withdrawal of the catheter tube 13. The location of the catheter tube 13 within the heart will depend upon the procedure to be carried out.

Figure 7:
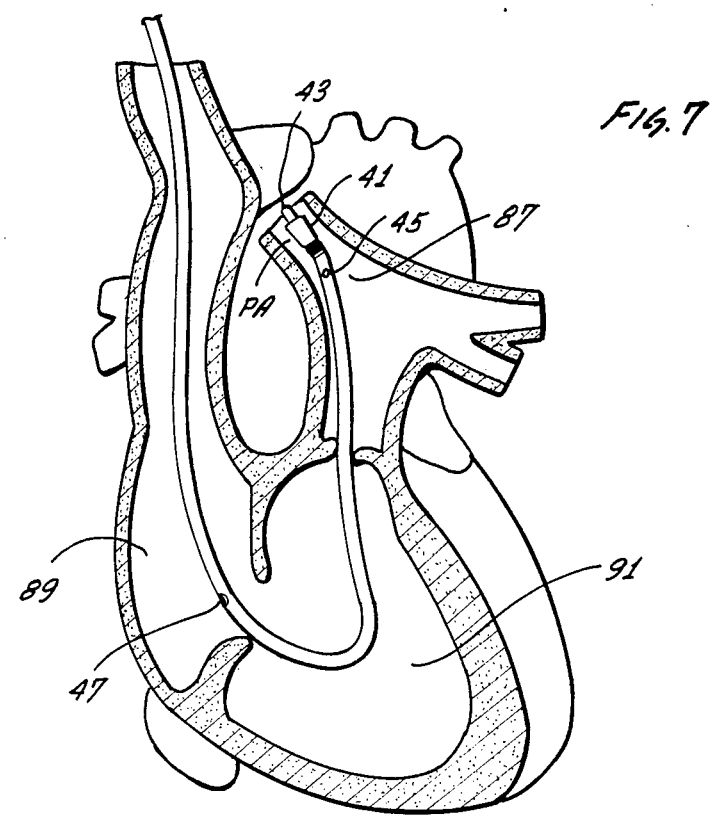
FIG. 7 is a sectional view of the human heart showing one example of how the apparatus of this invention can be used.

For example, to calculate ejection fraction, the catheter tube is inserted into the heart so as to place the injectate port 47 into the right atrium 89, the thermistor 45 into the pulmonary artery 87 and the distal port 43 into the pulmonary artery 87 as shown in FIG. 7. A bolus of cold fluid is then injected into the right atrium 89 through the injectate port 47 and allowed to mix with the bloodstream in the right ventricle 91. The blood and cold fluid mixture flow along the catheter tube 13 and over the thermistor 45 in the pulmonary artery 87. The temperature of the mixture changes with each heart beat, and the thermistor 45 can track each temperature change so as to provide a stepped temperature chart. This information can then be processed in accordance with known techniques to provide ejection fraction. Pressure can be mounted, if desired, through the through lumen 17.

Although an exemplary embodiment of the invention has been shown and described, many changes, modifications and substitutions may be made by one having ordinary skill in the art without necessarily departing from the spirit and scope of this invention.

I claim:

1. An apparatus for measuring the temperature of a fluid within a living body, said apparatus comprising:
   an elongated tube sized to be received within a vein or an artery and having proximal and distal ends, a peripheral wall, at least one lumen extending longitudinally within the tube and an opening in the peripheral wall which extends from the lumen to the exterior of the tube;
   a thermistor;
   a thermistor mounting body in said lumen adjacent said opening at least partially defining a cavity at said opening, said cavity opening radially outwardly; and
   said thermistor being partially within said mounting body and projecting radially outwardly of the mounting body into said cavity with the thermistor being spaced from the wall of the cavity over a major area thereof whereby the portion of the thermistor which projects into the cavity is in good heat transfer relationship to the fluid within the body.

2. An apparatus as defined in claim 1 including a relatively thin layer of electrical insulating material covering at least the portion of the thermistor which is in said cavity, said layer being substantially thinner than said mounting body.

3. An apparatus as defined in claim 1 wherein said thermistor has a major axis and a minor axis and is mounted with said major axis generally transverse to the longitudinal axis of the lumen at said thermistor.

4. An apparatus as defined in claim 1 wherein said tube has a body line and said thermistor extends radially outwardly in said cavity no farther than about said body line.

5. An apparatus as defined in claim 4 including a relatively thin layer of electrical insulating material covering at least the portion of the thermistor which is in said cavity, said thermistor has a major axis and a minor axis and is mounted with the major axis generally transverse to the longitudinal axis of the lumen at said thermistor.

6. An apparatus as defined in claim 5 including a lead coupled to the thermistor, said lead having an axial portion which extends along the lumen and a radial portion joined to the axial portion and extending generally transverse thereto at said cavity and joined to the thermistor.

7. An apparatus as defined in claim 5 including first and second plugs in said lumen on opposite sides of the mounting body, said mounting body at least assisting in retaining the plugs in the lumen.

8. An apparatus as defined in claim 1 including at least one thermistor lead coupled to the thermistor, said lead having an axial portion which extends along the lumen and a radial portion joined to the axial portion and extending generally transverse thereto at said cavity and joined to the thermistor.

9. An apparatus as defined in claim 1 wherein said mounting body covers no more than about one half of the exterior surface of the thermistor.

10. An apparatus as defined in claim 1 including first and second plugs in said lumen on opposite sides of the mounting body, said mounting body at least assisting in retaining the plugs in the lumen.

11. An apparatus as defined in claim 1 wherein said one lumen is a first lumen and said tube has a second lumen and a third lumen and said apparatus includes an inflatable balloon adjacent the distal end of the tube, said second lumen extends to the balloon to provide for balloon inflation, said third lumen is a through lumen and extends at least substantially to the distal end and opens at a distal port, and said first lumen is capable of injecting a fluid into the body, said peripheral wall having an injection port communicating with said first lumen proximity of said opening.

12. An apparatus for measuring the temperature of a fluid within a living body, said apparatus comprising:
   an elongated flexible tube sized to be received within a vein or an artery and having proximal and distal ends, a peripheral wall, at least one lumen extending longitudinally within the tube and an opening in the peripheral wall which extends from the lumen to the exterior of the tube;
   means for defining a cavity which opens generally radially outwardly at said opening;
   a thermistor mounted on said tube and projecting into said cavity with the thermistor being spaced from the wall of the cavity over a major area thereof; and said tube having a body line and said thermistor extending radially outwardly no farther than about said body line.

13. An apparatus as defined in claim 12 including a relatively thin layer of electrical insulating material covering at least the portion of the thermistor which is in said cavity.

14. An apparatus as defined in claim 12 wherein said thermistor has a major axis and a minor axis and is mounted with said major axis generally perpendicular to the longitudinal axis of the lumen at said thermistor.

15. An apparatus for measuring the temperature of a fluid flowing within the body, said apparatus comprising:
- an elongated tube sized to be received within a vein or an artery and to have the fluid flow along the tube, said tube having proximal and distal ends, a peripheral wall, at least one lumen extending longitudinally within the tube and an opening in the peripheral wall which extends from the lumen to the exterior of the tube;
- a thermistor having a major axis and a minor axis;
- means in said lumen for mounting said thermistor in a radially extending zone which includes said opening with said major axis extending generally transverse to the longitudinal axis of the lumen at said opening whereby said major axis is generally transverse to the fluid flowing along the tube; and
- at least a radial outward portion of the thermistor extending radially outwardly of said mounting means and being in good heat transfer relationship to the fluid flowing along the tube.

16. An apparatus as defined in claim 15 including a thin layer of electrical insulating material covering at least said radial outward portion of the thermistor.

17. An apparatus as defined in claim 15 wherein said tube has a body line and said thermistor extends radially outwardly no farther than about said body line.

18. An apparatus as defined in claim 15 including at least one thermistor lead coupled to the thermistor, said lead having an axial portion which extends along the lumen and a radial portion joined to the axial portion, said radial portion extends generally transverse to the axial portion at said cavity and is joined to the thermistor.

19. An apparatus as defined in claim 15 wherein said mounting means cooperates with said tube to at least partially define said cavity.

* * * * *